United States Patent [19]

Whittier

[11] Patent Number: 5,706,824

[45] Date of Patent: Jan. 13, 1998

[54] ENDOSCOPIC BIOPSY FORCEPS INSTRUMENT HAVING A CONSTANT FORCE SPRING BIASING THE JAWS CLOSED

[75] Inventor: John R. Whittier, Miami, Fla.

[73] Assignee: Symbiosis Corporation, Miami, Fla.

[21] Appl. No.: 650,316

[22] Filed: May 20, 1996

[51] Int. Cl.$^6$ ............................................ A61B 10/00
[52] U.S. Cl. ............................................ 128/751; 606/205
[58] Field of Search .............................. 128/749, 751, 128/752, 753, 754, 755, 756, 757, 656, 657, 658; 606/205, 206, 207, 208, 209, 167, 170, 174; 604/280, 281, 282

[56] References Cited

U.S. PATENT DOCUMENTS

| | | |
|---|---|---|
| 3,895,636 | 7/1975 | Schmidt . |
| 4,763,668 | 8/1988 | Macek et al. . |
| 4,945,920 | 8/1990 | Clossick . |
| 5,147,380 | 9/1992 | Hernandez et al. . |
| 5,228,451 | 7/1993 | Bales et al. . |
| 5,507,296 | 4/1996 | Bales et al. . |

*Primary Examiner*—Vincent Millin
*Assistant Examiner*—Robert N. Wieland
*Attorney, Agent, or Firm*—Finnegan, Henderson, Farabow, Garrett and Dunner, L.L.P.

[57] ABSTRACT

A biopsy forceps instrument includes a flexible coil having one or more pull wires extending therethrough, a clevis coupled to the distal end of the coil, a pair of forceps jaws mounted in the clevis and coupled to the distal end of the pull wire(s), and a proximal handle coupled to the proximal ends of the coil and the pull wires. The handle includes a slotted shaft and a displaceable spool having a cross member which extends through the slot. The shaft is coupled to the coil and the cross member is coupled to the pull wire(s). According to the invention, at least one constant force spring is provided between the shaft and the spool and biases the spool in the proximal direction in order to maintain the jaws in a closed position. According to a presently preferred embodiment of the invention, a pair of flat wound spiral springs are provided with the free flat ends of the springs being coupled to a proximal portion of the shaft. The distal portion of the spool is provided with a pair of cavities in which the spiral portions of the springs reside and a pair of grooves are provided on the interior of the spool through which the flattened spring extends. Alternative embodiments of the invention include one or two springs with the free flat end(s) coupled to either the spool or the shaft and the wound spiral end captured in a cavity or mounted on an axle.

15 Claims, 5 Drawing Sheets

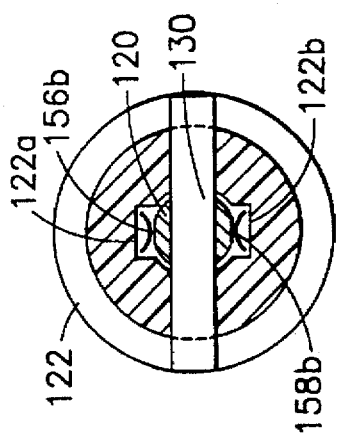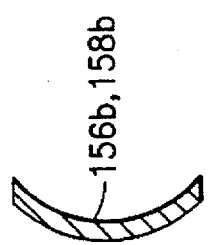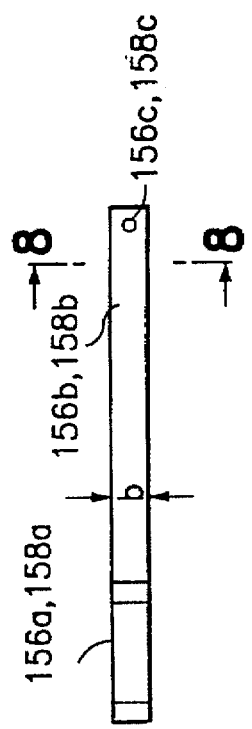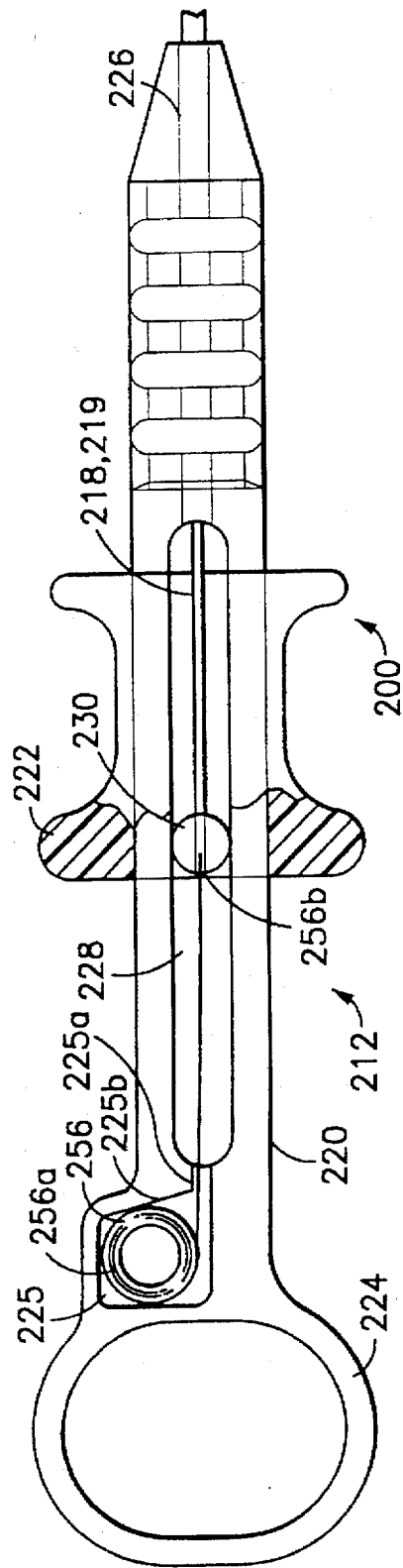
FIG.9
FIG.8
FIG.7
FIG.10

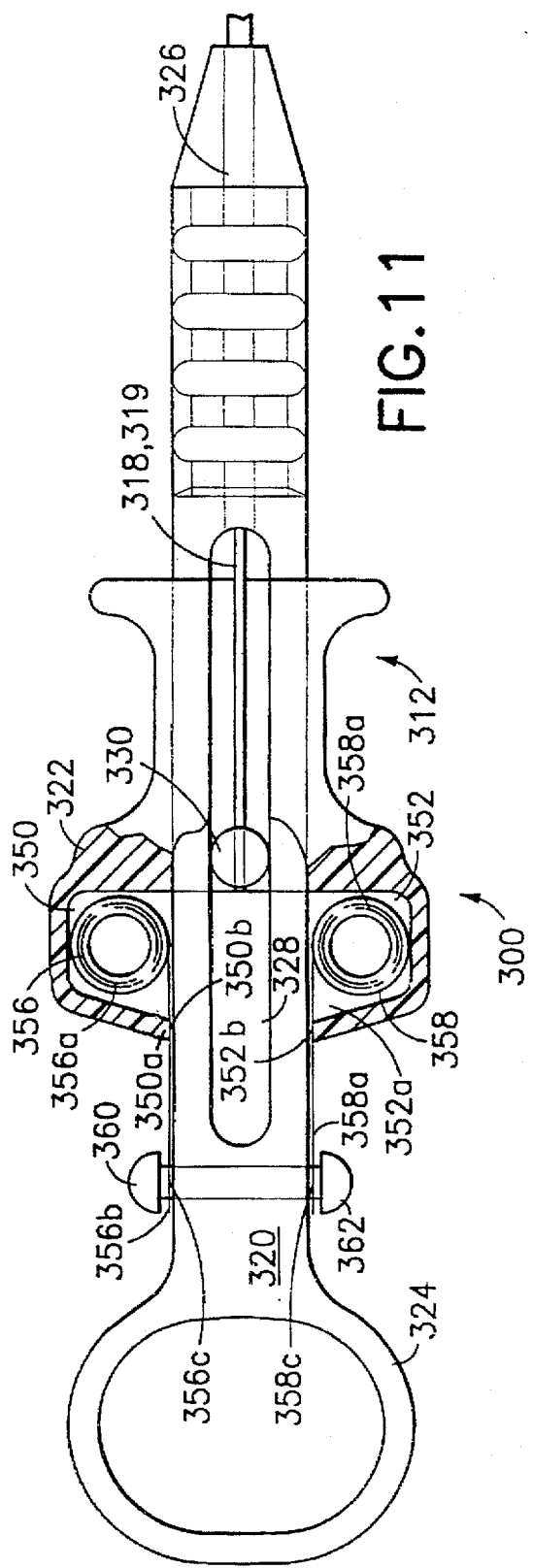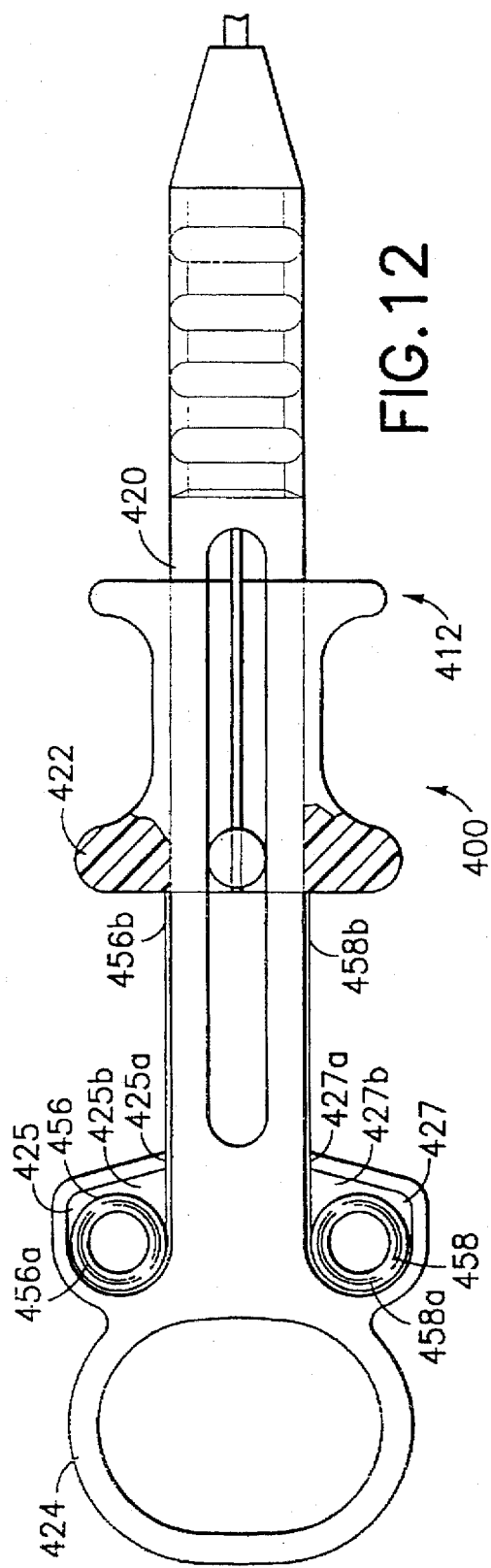

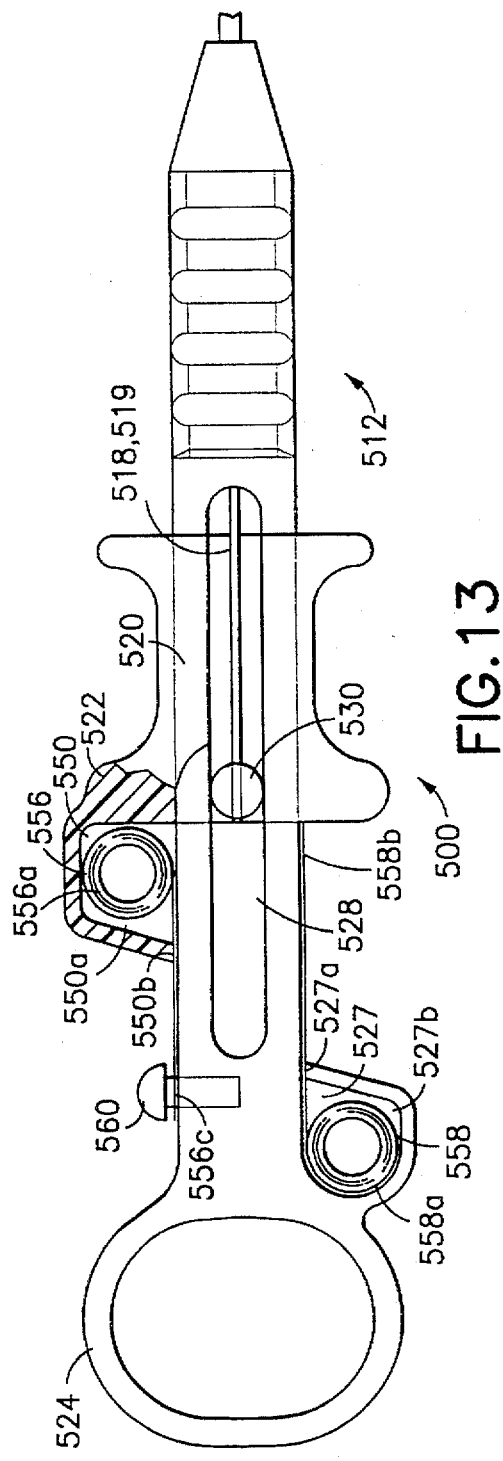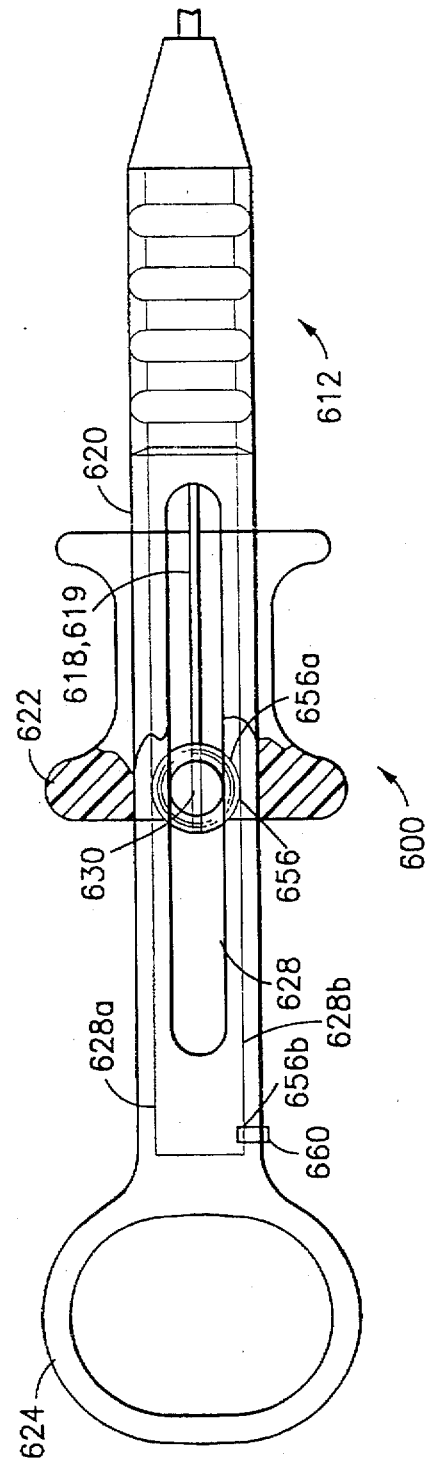

ENDOSCOPIC BIOPSY FORCEPS INSTRUMENT HAVING A CONSTANT FORCE SPRING BIASING THE JAWS CLOSED

This application is related to co-owned U.S. Pat. Nos. 5,507,296 and 5,228,451, the complete disclosures of which are hereby incorporated by reference herein.

BACKGROUND OF THE INVENTION

1. Field of the Invention

The invention relates to endoscopic biopsy forceps instruments. More particularly, the invention relates to an endoscopic biopsy forceps instrument having a constant force spring which biases the jaws of the biopsy forceps instrument closed.

2. State of the Art

Endoscopic biopsy forceps are used for taking tissue samples from the human body for analysis. A typical biopsy forceps instrument is shown in prior art FIGS. 1–3 and disclosed in co-owned U.S. Pat. No. 5,228,451, the complete disclosure of which is hereby incorporated by reference herein. The biopsy forceps instrument 10 generally includes a proximal handle 12 and a distal end effector assembly 14. A long flexible coil 16 having a pair of axially displaceable control wires 18, 19 extending therethrough couples the handle 12 and the end effector assembly 14. The coil 16 is preferably covered with a PTFE, FEP or polyolefin sheath 15 along substantially all of its length and/or a strain relief sleeve 17 covering a portion of the coil which extends from the handle 12. The proximal handle 12 includes a central shaft 20 and a displaceable spool 22. The proximal end of the shaft 20 is provided with a thumb ring 24 and a longitudinal bore 26 is provided at the distal end of the shaft 20. A longitudinal slot 28 extends from the proximal end of bore 26 to a point distal of the thumb ring 24. The proximal end of the coil 16 is coupled to the distal end of the bore 26 in the handle 12. The displaceable spool 22 is provided with a cross member 30 which passes through the slot 28 in the central shaft 20. The cross member 30 is provided with a coupling means 32 for attaching the proximal ends of the control wires 18, 19. The end effector assembly 14 includes a clevis 34 which is coupled to the distal end of the coil 16, and a pair of forceps jaws 36, 38 which are rotatably mounted in the clevis 34 by means of an axle pin 40. Each jaw 36, 38 is preferably provided with distal cutting teeth 36a, 38a and a proximal tang 36b, 38b. The proximal tangs 36b, 38b are each coupled to the distal end of a respective control wire 18, 19.

From the foregoing, those skilled in the art will appreciate that relative movement of the shaft 20 and spool 22 results in movement of the control wires 18, 19 relative to the coil 16. Such action results in opening and closing of the jaws 36, 38 as shown in prior art FIGS. 2 and 3.

The endoscopic biopsy procedure is accomplished through an endoscope which is inserted into a body and guided by manipulation to the biopsy site. The endoscope typically includes a long narrow flexible tube with an optical lens and a narrow lumen for receiving a biopsy forceps. The practitioner guides the endoscope to the biopsy site while looking through the optical lens and inserts the biopsy forceps through the lumen of the endoscope to the biopsy site. The path of the endoscope to the biopsy site is usually long and tortuous. As the distal end of the forceps instrument passes through the endoscope, it is preferable that the jaws be held in the closed position to minimize friction between the interior of the lumen of the endoscope and the jaws.

After the jaws are delivered to the biopsy site, the practitioner manipulates the actuating handle to effect a tissue sampling operation at the distal end of the instrument while viewing the biopsy site through the optical lens of the endoscope. In many instances, it is incumbent on the practitioner to take care that too much force not be applied to the jaws as the sample is taken. After a sample has been obtained, the practitioner and/or an assistant carefully withdraws the instrument from the endoscope. When the jaws are removed from the endoscope, they are carefully opened and the tissue sample is removed from the jaws for tissue analysis. It is important to keep the jaws closed while removing them from the endoscope lest the sample be lost.

From the foregoing, therefore, it will be appreciated that it is desirous to keep the biopsy forceps jaws in the closed position at all times except for the taking of the sample and the subsequent removal of the sample from the jaws. In order to maintain the forceps jaws in a closed position, it is known in the art to provide a coil compression spring in the handle assembly of the forceps instrument in order to bias the spool in a proximal direction. See, e.g., U.S. Pat. No. 4,763,668 to Macek et al. This maintains the jaws in a closed position until the spool is moved against the spring by the practitioner. State of-the-art spring biased forceps have the disadvantage that the force exerted by the spring varies significantly as the forceps instrument is guided through the lumen of the endoscope. More specifically, as the instrument is guided through a tortuous path, the length of the coil increases due to bending. As the length of the coil is increased, the clevis is moved distally from the handle and the pull wires are pulled distally as well. This causes the spool to be moved distally against the coil spring. Since the spring obeys Hooke's Law (F=−kx), the force (F) exerted by the spring against the spool is in direct proportion to the spool displacement (x) which is increased by the increase in length (Δx) of the coil. Thus, when the jaws are in position to obtain a sample, the force exerted by the spring can be so great that it is difficult to open the jaws. Choosing a different spring constant (k) is difficult because the spring must still exert sufficient force to keep the jaws closed when the coil is straightened.

SUMMARY OF THE INVENTION

It is therefore an object of the invention to provide an endoscopic biopsy forceps instrument having a spring which biases the forceps jaws to a closed position.

It is also an object of the invention to provide an endoscopic biopsy forceps instrument having a spring which exerts a substantially constant force regardless of the spool displacement.

In accord with these objects which will be discussed in detail below, the biopsy forceps instrument of the present invention includes a flexible coil having one or more pull wires extending therethrough, a jaw assembly including a pair of forceps jaws, the jaw assembly being coupled to the distal end of the flexible coil and the pull wire(s), and a proximal handle coupled to the proximal ends of the coil and the pull wires. The handle includes a slotted shaft and a displaceable spool having a cross member which extends through the slot. The shaft is coupled to the coil and the cross member is coupled to the pull wire(s). According to the invention, at least one constant force spring is provided which is coupled to either or both of the shaft and the spool and which biases the spool in the proximal direction in order to maintain the jaws in a closed position. According to a presently preferred embodiment of the invention, a pair of flat wound spiral springs with free ends are provided with the free ends of the springs being coupled to a proximal portion of the shaft. The distal portion of the spool is provided with a pair of cavities in which the spiral portions of the springs reside and a pair of grooves are provided on the interior of the spool through which the flattened spring extends. Alternative embodiments of the invention include one or two springs with the free flat end(s) coupled to either the spool or the shaft and the wound spiral end captured in a cavity or mounted on an axle. Additional objects and advantages of the invention will become apparent to those skilled in the art upon reference to the detailed description taken in conjunction with the provided figures.

BRIEF DESCRIPTION OF THE DRAWINGS

FIG. 7 is a bottom view of the spring of FIG. 6;

FIG. 8 is a sectional view taken along line 8—8 in FIG. 7;

FIG. 9 is a sectional view taken along line 9—9 in FIG. 4;

FIG. 10 is a view similar to FIG. 4 of a second embodiment of the invention;

FIG. 11 is a view similar to FIG. 10 of a third embodiment of the invention;

FIG. 12 is a view similar to FIG. 11 of a fourth embodiment of the invention;

FIG. 13 is a view similar to FIG. 12 of a fifth embodiment of the invention; and FIG. 14 is a view similar to FIG. 13 of a sixth embodiment of the invention.

DETAILED DESCRIPTION OF THE PREFERRED EMBODIMENTS

Figure 1:
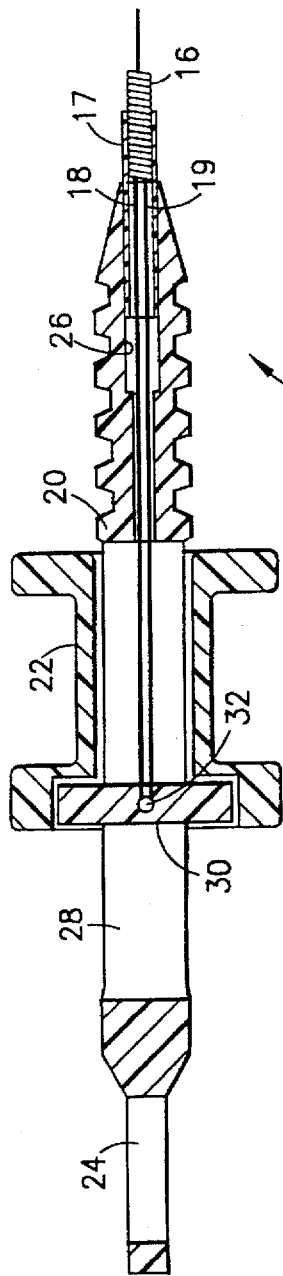
FIG. 1 is a broken side elevation view in partial section of the proximal end of a prior art biopsy forceps instrument.
Figure 2:
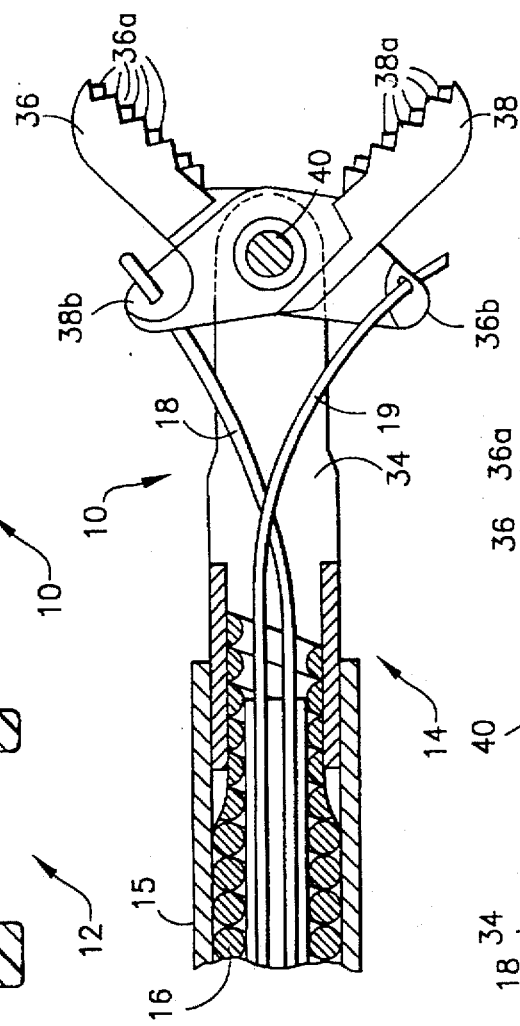
FIG. 2 is an enlarged broken side elevation view in partial section of the distal end of a prior art biopsy forceps instrument with the jaws in the open position.
Figure 3:
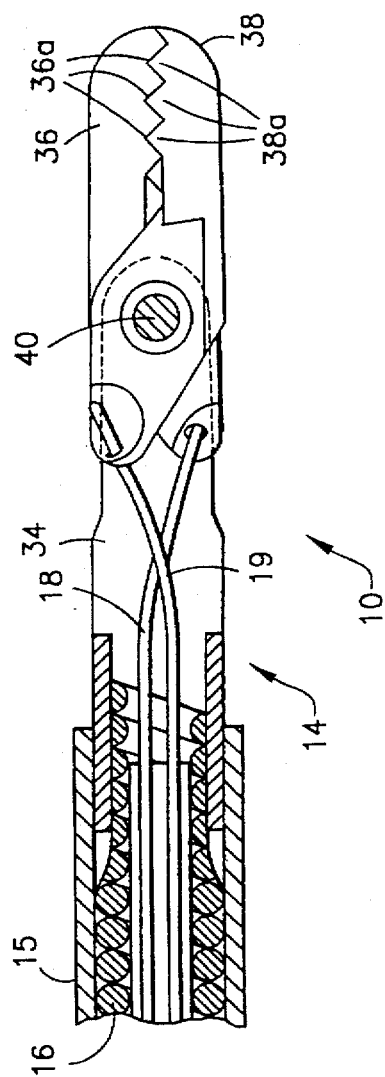
FIG. 3 is an enlarged broken side elevation view in partial section of the distal end of a prior art biopsy forceps instrument with the jaws in the closed position.
Figure 4:
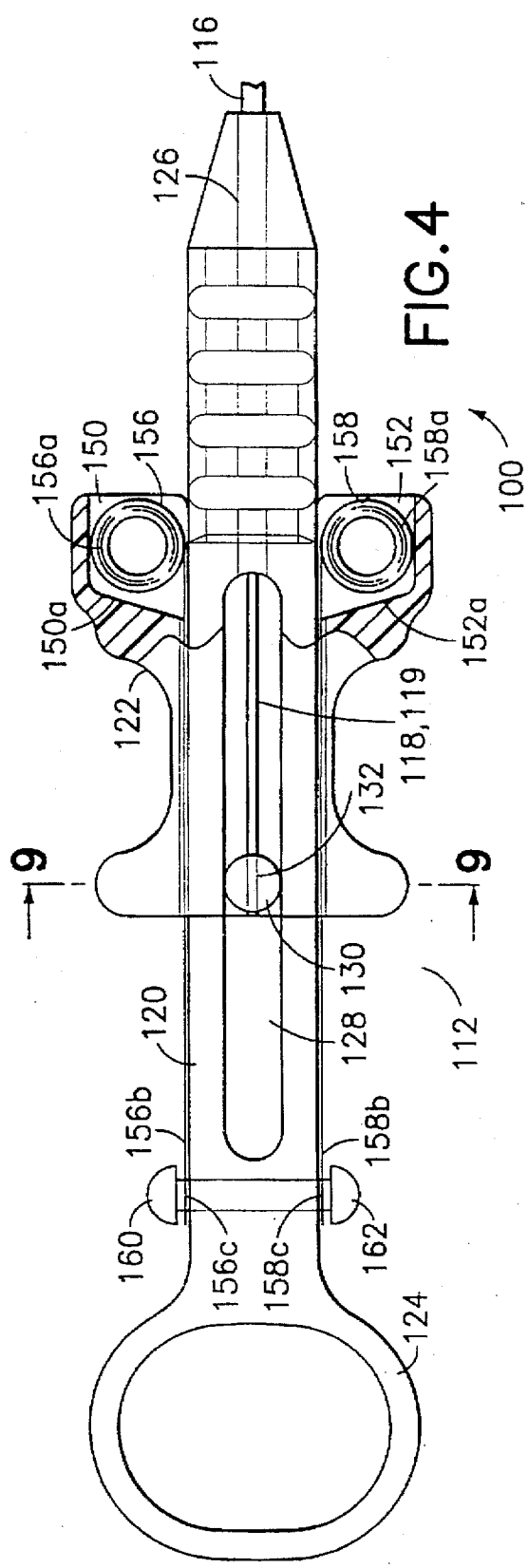
FIG. 4 is a broken transparent top view of the proximal end of a first embodiment of a biopsy forceps instrument using a pair of constant force springs according to the invention.
Figure 6:
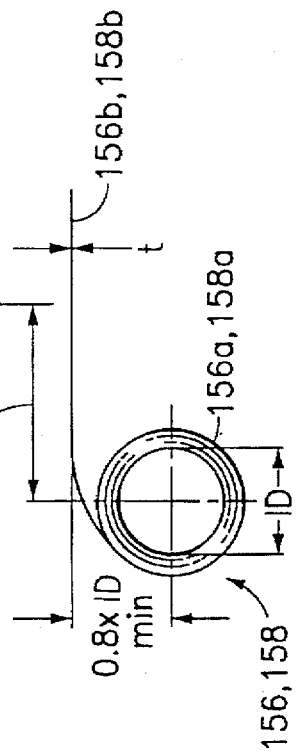
FIG. 6 is a side elevation view of the spring of FIG. 5.
Figure 5:
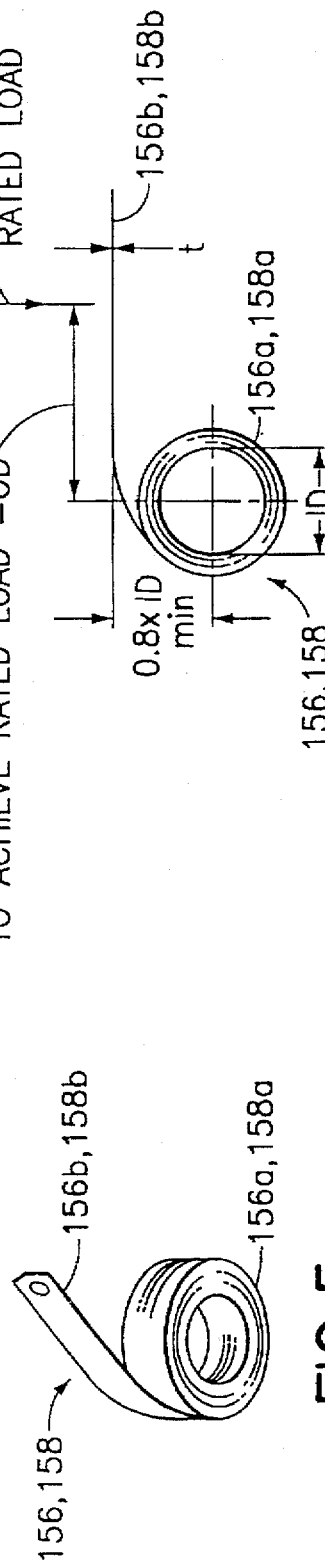
FIG. 5 is a perspective view of one of the constant force springs of FIG. 4.

Referring now to FIG. 4, an endoscopic biopsy forceps instrument 100 according to the invention includes a proximal handle 112 and a distal end effector assembly which is substantially the same as the prior art end effector assembly 14 shown in FIGS. 2 and 3. A long flexible coil 116 having a pair of axially displaceable control wires 118, 119 extending therethrough couples the handle 112 and the end effector assembly. The proximal handle 112 includes a central shaft 120 and a displaceable spool 122. The proximal end of the shaft 120 is provided with a thumb ring 124 and a longitudinal bore 126 is provided at the distal end of the shaft 120. A longitudinal slot 128 extends from the proximal end of bore 126 to a point distal of the thumb ring 124. The proximal end of the coil 116 is coupled to the distal end of the bore 126 in the handle 112 preferably as taught by previously incorporated U.S. Pat. No. 5,507,296. The displaceable spool 122 is provided with a cross member 130 which passes through the slot 128 in the central shaft 120. The cross member 130 is provided with a coupling means 132 for attaching the proximal ends of the control wires 118, 119.

According to a first embodiment of the invention, the spool 122 is provided with a pair of distal wells 150, 152 each of which houses the coiled portion 156a, 158a of a constant force spring 156, 158 in a manner in which the springs are free to unwind. As shown, each well 150, 152 has an inclined proximal wall 150a, 152a which is angled approximately 105° distally. Each of the springs 156, 158 has a free flat end 156b, 158b which extends between the spool 122 and the shaft 120 and is fastened to the shaft 120 near the thumb ring 124 with a rivet 160, 162. As explained in more detail below, the springs 156, 158 bias the spool 122 towards the thumb ring 124. According to a presently preferred embosiment, each spring 156, 158 exerts a substantially constant force of approximately one half pound. A suitable spring is available as part number A-CFS-050 from Small Parts, Inc., Miami Lakes, Fla. The spring has a thickness of approximately 0.004 inches, a width of approximately 0.25 inches, and an uncoiled length of approximately 15.0 inches. Other suitable springs are available from Vulcan Spring & Mfg. Co., Telford, Pa. (models BB, BC, BD, BE, HD, HE, JD, JE, KD, KE, LD, LE, FED, ME, ND, NE, TA, TB, TC, TD), and Springtec Corporation, Kulpsville, Pa. (models 3CFS37 and 3CFS49).

Turning now to FIGS. 5–8, a constant force spring 156, 158 used in the invention is made from a substantially flat strip of material such as spring steel which is wound into a spiral 156a, 158a, leaving a free flat end 156b, 158b. The free end is preferably provided with a hole 156c, 158c for coupling the spring to the shaft 120 as shown in FIG. 4, for example. After the spring is wound, unwinding of the spiral exerts a relatively constant force throughout a relative large range of displacement. The rated load of the spring is not reached until after an initial deflection of approximately 1.25 times the inner diameter of the coil. In addition, as the spring is unwound, the flat end 156b, 158b tends to bow inward toward the spiral 156a, 158a as shown in FIG. 8.

Turning now to FIG. 9, the spool 122 of the instrument 100 described above is preferably provided with a pair of interior grooves 122a, 122b through which the bowed ends 156b, 158b of the springs 156, 158 freely pass so that movement of the spool relative to the shaft is not impeded. The depth of the grooves 122a, 122b is preferably approximately ten times the thickness "t" (FIG. 6) of the flat spring material.

As mentioned above, one or more constant force springs may be used to obtain a constant force closing the forceps jaws regardless of the displacement of the spool. Moreover, the free end of the spring may be coupled to either the shaft or the spool.

Turning now to FIG. 10, a second embodiment of a biopsy forceps instrument 200 according to the invention includes a handle 212 having a central shaft 220 and a displaceable spool 222. The shaft 220 has a proximal thumb ring 224, a distal bore 226, and a central slot 228. The spool 222 has a cross member 230 which passes through the slot 228 and is coupled to the pull wires 218, 219. According to this embodiment, the shaft 220 is provided with a spring well 225 adjacent to the thumb ring 224. The well has a distal outlet 225a which enters the central slot 228 of the shaft. The wound end 256a of a constant force spring 256 is disposed in the well 225 such that the free end 256b of the spring exits the outlet 225a, enters the slot 228, and is coupled to the cross member 230 of the spool 222. In order to facilitate rotation of the wound portion 256a of the spring 256, the well 225 has and inclined distal wall 225b which is angled approximately 105° toward the distal outlet 225a.

FIG. 11 shows a third embodiment of a biopsy forceps instrument 300 according to the invention in which similar reference numerals refer to features which are similar to the features of the first two embodiments described above. According to this embodiment, the spool 322 is provided with two proximal spring wells 350, 352 each of which has a proximally inclined inner wall 350a, 352a which is angled toward a proximal outlet 350b, 352b which is adjacent to the central shaft 320. The wound end 356a, 358a of a constant force spring 356, 358 is disposed in each well 350, 352 such that the free end 356b, 358b exits the outlet 350b, 352b. The ends of the springs are attached to the shaft 320 by rivets 360, 362 as described above with reference to FIG. 4.

A fourth embodiment of a biopsy forceps instrument 400 is shown in FIG. 12 in which similar reference numerals refer to features which are similar to the features of the three embodiments described above. According to the embodiment of FIG. 12, the shaft 420 is provided with a pair of spring wells 425, 427 adjacent to the thumb ring 424. Each well has a distal outlet 425a, 427a which is adjacent to the exterior of the central slot 428 portion of the shaft 420. The wound ends 456a, 458a of constant force springs 456, 458 are disposed in the wells 425, 427 such that the free ends 456b, 458b of the springs exit the outlets 425a, 427a, extend along the outer surface of the shaft and are coupled to a proximal portion of the spool 422. In order to facilitate rotation of the wound portions of the springs 456, 458, the wells 425, 427 have inclined distal walls 425b, 427b which are angled approximately 105° toward the distal outlets.

A fifth embodiment of the invention is shown in FIG. 13 in which similar reference numerals refer to features which are similar to the features of the four embodiments described above. It will be appreciate that in this embodiment, one spring 556 is arranged like the spring 356 described in FIG. 11 and another spring 558 is arranged like the spring 458 described in FIG. 12.

A sixth embodiment of the invention is shown in FIG. 14 in which similar reference numerals refer to features which are similar to the features of the four embodiments described above. According to the embodiment of FIG. 14, the central shaft 620 is provided with interior grooves 628a, 628b adjacent to the central slot 628 and the wound end 656a of a constant force spring 656 is rotatably mounted on the cross member 630 of the spool 622. The interior grooves 628a, 628b are provided to receive the spring and allow the spring to move proximally and distally. The free end 656b of the spring is attached to a proximal portion of the handle 612 with a rivet 660.

There have been described and illustrated herein several embodiments of an endoscopic biopsy forceps instrument having a constant force spring which biases the forceps jaws closed. While particular embodiments of the invention have been described, it is not intended that the invention be limited thereto, as it is intended that the invention be as broad in scope as the art will allow and that the specification be read likewise. Thus, while particular spring wells have been disclosed, it will be appreciated that other spring wells could be utilized. For example, the spring wells shown are substantially rectilinear with an inclined wall. However, circular or semicircular spring wells could be used and concave walls could be used in place of inclined walls. While not necessarily preferred, rectilinear spring wells with orthogonal walls could also be used. In addition, it may be desirable to mount the wound portions of the springs on axle drums so that the springs rotate about an axle as they unwind. Also, while free ends of springs have been shown to be attached to the forceps handle with rivets, it will be recognized that other types of fasteners could be used with similar results obtained. In addition, while instruments having both a single spring and a pair of springs have been shown, the instruments with two springs are presently preferred as they provide a more even distribution of force. It will therefore be appreciated by those skilled in the art that yet other modifications could be made to the provided invention without deviating from its spirit and scope as so claimed.

I claim:

1. An endoscopic biopsy forceps instrument comprising:

a) a flexible coil having a proximal and a distal end;

b) at least one control wire having a proximal and a distal end and extending through said flexible coil;

c) actuation means coupled to said proximal end of said flexible coil and said proximal end of said at least one control wire for displacing one of said flexible coil and said at least one control wire relative to the other; and d) a jaw assembly including a pair of forceps jaws, said jaw assembly being coupled to said distal ends of said coil and said control wire such that said jaws are movable from an open position to a closed position, wherein said actuation means further includes at least one constant force spring which biases said jaws to said closed position.

2. An endoscopic biopsy forceps instrument according to claim 1, wherein:

said at least one constant force spring is a wound spiral having a free end.

3. An endoscopic biopsy forceps instrument according to claim 2, wherein:

said actuation means includes a central shaft and a displaceable spool, one of said shaft and spool being coupled to said proximal end of said flexible coil and the other of said shaft and spool being coupled to said proximal end of said at least one control wire, said free end of said constant force spring being coupled to one of said shaft and spool and said wound spiral being rotatably coupled to the other of said shaft and spool.

4. An endoscopic biopsy forceps instrument according to claim 3, wherein:

said free end is coupled to said shaft and said spool has a spring well in which said wound spiral is rotatably disposed.

5. An endoscopic biopsy forceps instrument according to claim 4, wherein:

said spring well is disposed at a distal portion of said spool.

6. An endoscopic biopsy forceps instrument according to claim 5, wherein:

said spring well has an inclined proximal surface.

7. An endoscopic biopsy forceps instrument according to claim 5, wherein:

said spool has an interior groove through which said spring passes.

8. An endoscopic biopsy forceps instrument according to claim 4, wherein:

said spring well is disposed at a proximal portion of said spool.

9. An endoscopic biopsy forceps instrument according to claim 8, wherein:

said spring well has an inclined proximal surface.

10. An endoscopic biopsy forceps instrument according to claim 3, wherein:

said free end is coupled to said spool and said shaft has a spring well in which said wound spiral is rotatably disposed.

11. An endoscopic biopsy forceps instrument according to claim 10, wherein:

said spring well has an inclined distal surface.

12. An endoscopic biopsy forceps instrument according to claim 10, wherein:

said shaft has a central slot, said spool has a cross member which passes through said central slot, and said free end is coupled to said cross member.

13. An endoscopic biopsy forceps instrument according to claim 3, wherein:

said shaft has a central slot, said spool has a cross member which passes through said central slot, said free end is coupled to said shaft and said wound spiral is rotatably disposed on said cross member.

14. An endoscopic biopsy forceps instrument according to claim 1, wherein:

said at least one constant force spring comprises first and second constant force springs.

15. An endoscopic biopsy forceps instrument according to claim 14, wherein:

said first and second constant force springs each exert a force of approximately one half pound.

* * * * *